United States Patent
Glukhovsky et al.

(10) Patent No.: US 7,604,589 B2
(45) Date of Patent: Oct. 20, 2009

(54) DEVICE, SYSTEM AND METHOD FOR DETERMINING ORIENTATION OF IN-VIVO DEVICES

(75) Inventors: Arkady Glukhovsky, Santa Clarita, CA (US); Gavriel Meron, Petach Tikva (IL); Alex Blijevsky, Zichron Yaakov (IL)

(73) Assignee: Given Imaging, Ltd., Yoqneam (IL)

( * ) Notice: Subject to any disclaimer, the term of this patent is extended or adjusted under 35 U.S.C. 154(b) by 646 days.

(21) Appl. No.: 10/950,694

(22) Filed: Sep. 28, 2004

(65) Prior Publication Data
US 2005/0107666 A1 May 19, 2005

Related U.S. Application Data

(60) Provisional application No. 60/507,132, filed on Oct. 1, 2003.

(51) Int. Cl.
*A61B 1/00* (2006.01)
(52) U.S. Cl. .................. 600/117; 600/109; 600/160
(58) Field of Classification Search .............. 600/476, 600/473, 309, 542, 160, 350; 348/74; 73/178 R, 73/5.43; 33/366
See application file for complete search history.

(56) References Cited

U.S. PATENT DOCUMENTS

| | | | |
|---|---|---|---|
| 3,322,374 A | 5/1967 | King, Jr. | |
| 3,866,602 A * | 2/1975 | Furihata | .............. 600/103 |
| 3,971,362 A | 7/1976 | Pope et al. | |
| 4,219,821 A | 8/1980 | Selim | |
| 4,239,040 A | 12/1980 | Hosoya et al. | |
| 4,246,792 A | 1/1981 | Matzuk | |
| 4,278,077 A | 7/1981 | Mizumoto | |
| 4,429,328 A | 1/1984 | Jones, Jr. et al. | |
| 4,431,005 A | 2/1984 | McCormick | |
| 4,439,197 A | 3/1984 | Honda et al. | |
| 4,646,724 A | 3/1987 | Sato et al. | |
| 4,651,201 A | 3/1987 | Schoolman | |

(Continued)

FOREIGN PATENT DOCUMENTS

DE 34 40 177 6/1986

(Continued)

OTHER PUBLICATIONS

U.S. Appl. No. 09/807,892, filed Jun. 6, 2001, Meron et al.

(Continued)

*Primary Examiner*—Eric F Winakur
*Assistant Examiner*—Lawrence N Laryea
(74) *Attorney, Agent, or Firm*—Pearl Cohen Zedek Latzer, LLP (57) ABSTRACT

A system and method may determine the orientation of an in-vivo imaging device relative to the earth's gravitation field. Some embodiments may enable indication of specific locations where other methods provide non-satisfactory imaging coverage. The system may include an in-vivo imaging system with a container or shell containing an orientation object. The container may be placed in at least one optical dome or optical field of an in-vivo imaging device, such as an autonomous capsule. The location of the orientation object's image on the in-vivo imaging device imager, as well as size of the image, may be determined as functions of the location of the orientation object inside the container, for each image acquired.

17 Claims, 7 Drawing Sheets

U.S. PATENT DOCUMENTS

| | | | |
|---|---|---|---|
| 4,656,508 | A | 4/1987 | Yokota |
| 4,689,621 | A | 8/1987 | Kleinberg |
| 4,793,348 | A * | 12/1988 | Palmaz ...................... 606/194 |
| 4,803,992 | A | 2/1989 | Lemelson |
| 4,819,620 | A | 4/1989 | Okutsu |
| 4,844,076 | A | 7/1989 | Lesho et al. |
| 5,042,486 | A | 8/1991 | Pfeiler et al. |
| 5,187,572 | A | 2/1993 | Nakamura et al. |
| 5,211,165 | A | 5/1993 | Dumoulin et al. |
| 5,217,449 | A | 6/1993 | Yuda et al. |
| 5,233,984 | A * | 8/1993 | Thompson ................... 607/18 |
| 5,267,033 | A | 11/1993 | Hoshino |
| 5,279,607 | A | 1/1994 | Schentag et al. |
| 5,330,427 | A | 7/1994 | Weissenburger |
| 5,395,366 | A | 3/1995 | D'Andrea et al. |
| 5,398,670 | A | 3/1995 | Ortiz et al. |
| 5,429,132 | A | 7/1995 | Guy et al. |
| 5,459,605 | A | 10/1995 | Kempf |
| 5,495,114 | A | 2/1996 | Adair |
| 5,515,853 | A | 5/1996 | Smith et al. |
| 5,563,071 | A | 10/1996 | Augurt |
| 5,592,180 | A | 1/1997 | Yokev et al. |
| 5,604,531 | A | 2/1997 | Iddan |
| 5,681,260 | A | 10/1997 | Ueda |
| 5,697,377 | A | 12/1997 | Wittkampf |
| 5,736,958 | A | 4/1998 | Turpin |
| 5,742,331 | A * | 4/1998 | Uomori et al. ................. 348/51 |
| 5,747,996 | A | 5/1998 | Fuchs |
| 5,764,809 | A | 6/1998 | Nomami et al. |
| 5,796,861 | A | 8/1998 | Vogt et al. |
| 5,819,736 | A | 10/1998 | Avny et al. |
| 5,913,820 | A | 6/1999 | Bladen et al. |
| 5,929,901 | A | 7/1999 | Adair et al. |
| 5,984,640 | A * | 11/1999 | Wang ..................... 416/244 R |
| 5,986,693 | A | 11/1999 | Adair et al. |
| 5,993,378 | A | 11/1999 | Lemelson |
| 6,043,839 | A | 3/2000 | Adair et al. |
| 6,099,482 | A | 8/2000 | Brune et al. |
| 6,149,581 | A | 11/2000 | Klingenstein |
| 6,188,355 | B1 | 2/2001 | Gilboa |
| 6,233,476 | B1 | 5/2001 | Strommer et al. |
| 6,240,312 | B1 | 5/2001 | Alfano et al. |
| 6,254,548 | B1 | 7/2001 | Ishikawa et al. |
| 6,304,769 | B1 | 10/2001 | Arenson et al. |
| 6,324,418 | B1 | 11/2001 | Crowley et al. |
| 6,447,448 | B1 | 9/2002 | Ishikawa et al. |
| 6,453,190 | B1 | 9/2002 | Acker et al. |
| 6,580,938 | B1 | 6/2003 | Acker |
| 6,632,175 | B1 | 10/2003 | Marshall |
| 6,689,056 | B1 | 2/2004 | Kilcoyne et al. |
| 6,690,963 | B2 | 2/2004 | Ben-Haim et al. |
| 6,692,430 | B2 | 2/2004 | Adler |
| 6,709,387 | B1 | 3/2004 | Glukovsky et al. |
| 7,066,879 | B2 * | 6/2006 | Fowler et al. ............... 600/102 |
| 7,192,397 | B2 * | 3/2007 | Lewkowicz et al. ......... 600/160 |
| 2001/0035902 | A1 | 11/2001 | Iddan et al. |
| 2002/0103417 | A1 | 8/2002 | Gazdzinski |
| 2002/0109774 | A1 | 8/2002 | Meron |
| 2002/0165592 | A1 | 11/2002 | Glukovsky et al. |
| 2002/0173718 | A1 | 11/2002 | Frisch et al. |
| 2002/0177779 | A1 | 11/2002 | Adler et al. |
| 2003/0018280 | A1 | 1/2003 | Lewkowicz et al. |
| 2003/0043263 | A1 | 3/2003 | Glukovsky et al. |
| 2003/0077223 | A1 | 4/2003 | Glukovsky et al. |
| 2003/0117491 | A1 | 6/2003 | Avni et al. |
| 2003/0135115 | A1* | 7/2003 | Burdette et al. ............. 600/437 |
| 2003/0151661 | A1 | 8/2003 | Davidson et al. |
| 2003/0164952 | A1* | 9/2003 | Deichmann et al. ......... 356/603 |
| 2003/0167000 | A1 | 9/2003 | Mullick et al. |
| 2003/0174208 | A1 | 9/2003 | Glukovsky et al. |
| 2003/0195415 | A1 | 10/2003 | Iddan |
| 2003/0204962 | A1* | 11/2003 | Mangerson ............... 33/366.15 |
| 2003/0208107 | A1* | 11/2003 | Refael ........................ 600/300 |
| 2003/0214579 | A1 | 11/2003 | Iddan |
| 2003/0216622 | A1 | 11/2003 | Meron et al. |
| 2004/0087832 | A1 | 5/2004 | Glukovsky et al. |
| 2006/0004255 | A1* | 1/2006 | Iddan et al. ................. 600/160 |

FOREIGN PATENT DOCUMENTS

| | | |
|---|---|---|
| FR | 2 688 997 | 10/1993 |
| IL | 143259 | 5/2001 |
| JP | 4144533 | 5/1992 |
| JP | 6114037 | 4/1994 |
| JP | 6114064 | 4/1994 |
| JP | 6154191 | 6/1994 |
| JP | 6285044 | 10/1994 |
| JP | 111985 | 5/1995 |
| JP | 7255692 | 10/1995 |
| JP | 2000-342522 | 12/2000 |
| JP | 2001046358 | 2/2001 |
| JP | 2001-095756 | 4/2001 |
| JP | 2001-104241 | 4/2001 |
| JP | 2001-104243 | 4/2001 |
| JP | 2001-104244 | 4/2001 |
| JP | 2001-104287 | 4/2001 |
| JP | 2001-112709 | 4/2001 |
| JP | 2001-112710 | 4/2001 |
| JP | 2001091880 | 4/2001 |
| JP | 2001095755 | 4/2001 |
| JP | 2001104242 | 4/2001 |
| JP | 2001112740 | 4/2001 |
| JP | 2001-137182 | 5/2001 |
| JP | 2001-231744 | 8/2001 |
| JP | 2001231186 | 8/2001 |
| JP | 2001231187 | 8/2001 |
| JP | 2001245844 | 9/2001 |
| JP | 2002000556 | 1/2002 |
| WO | WO 00-10456 | 3/2000 |
| WO | WO 00/22975 | 4/2000 |
| WO | WO 01-06917 | 2/2001 |
| WO | WO 01-50941 | 7/2001 |
| WO | WO 01/69212 | 9/2001 |
| WO | WO 02/55126 | 7/2002 |
| WO | WO 02/094337 | 11/2002 |
| WO | WO 2004/028336 | 4/2004 |
| WO | WO 2004/035106 | 4/2004 |
| WO | WO 2004/036803 | 4/2004 |

OTHER PUBLICATIONS

U.S. Appl. No. 10/166,025, filed Jun. 11, 2002, Lewkowicz et al.
U.S. Appl. No. 10/213,345, filed Aug. 7, 2002, Glukovsky.
Heidelberger Kapsel—ein Kleinstsender fur die pH-Messung im Magen Lange et al. Telefunken-Zeitung Ig 36 (1963) Haft 5 pp. 265-270.
New smart plastic has good memory—Turke.
Robots for the future—Shin-ichi, et al.
The Radio Pill, Rowlands, et al British Communications and Electronics, Aug. 1960, pp. 598-601.
Video Camera to "TAKE"—RF System Lab, Dec. 25, 2001.
Wellesley company sends body monitors into space—Crum.
www rfnorkla com—NORIKA3, Dec. 24, 2001.
Wireless transmission of a color television moving image from the stomach using a miniature CCD camera light source and microwave transmitter Swain CP Gong F Mills TN GastroIntest Endosc 1997;45:AB40.
In Pursuit of the Ultimate Lamp, Craford et al , Scientific American, Feb. 2001.
Manual of Photogrammetry Thompson (Ed.), Third Edition vol. Two, American Society of Photogrammetry.
Machine Vision: Theory, Algorithms, Practicalities—E R Davies.
www Jason net—Tlny cam, © 2000.
www middleeasthealthmag com—Review proves the value of computers.

www.pedinc.com Personal electronic devices © 1997.

BBC News Online—Pill camera to broadcast from the gut . Feb. 21, 2000 www.news.bbc.co.uk.

Nam, et al , A method for Position Detection of the wireless capsule endoscopes Module Using the Solution of Nonlinear Simultaneous Equations , Sensors Conference 2002, p. 377.

Nam, et al , A method for Position Detection of Miniaturized Telemetry Module Using the Solution of Nonlinear Simultaneous Equations , 2002.

Park, et al , "A Technique for Localization of Biomedical Telemetry Sensor in Human Body" Proceedings of the International Sensor Conference 2001 Seoul, Korea.

Localization of a wireless capsule endoscope In the GI Tract Gastrointestinal Endoscopy 2001;53:AB126.

Park, et al, "A Technique for Position Detection Of Miniatured Wireless Telemetry Module In the Human Body" Proceedings of the 32nd ISR (International Symposium on Robotics) Apr. 19-21 2001 pp. 1888-1892.

Park et al "Design of Bi-directional and Multi-Channel Miniaturized Telemetry Module for Wireless Endoscopy" 2nd Annual International IEEE-EMBS Special Topic Conference on Microtechnologies in Medicine &Biology, May 2-4, 2002, Madison, Wisconsin USA pp. 273-276.

Park et al "Design of Miniaturized Telemetry Module for Bi-Directional Wireless Endoscopy" May 2-4, 2002.

* cited by examiner

DEVICE, SYSTEM AND METHOD FOR DETERMINING ORIENTATION OF IN-VIVO DEVICES

RELATED APPLICATION DATA

This application claims benefit from U.S. provisional application Ser. No. 60/507,132, filed on Oct. 1, 2003, entitled SYSTEM, APPARATUS AND METHOD FOR MEASUREMENT OF MOTION PARAMETERS OF AN IN-VIVO DEVICE which is incorporated in its entirety by reference herein.

FIELD OF THE INVENTION

The present invention relates to methods and devices useful in in-vivo imaging. Specifically, embodiments of the present invention relate to systems and methods that enable determining of the orientation of in-vivo imaging devices.

BACKGROUND OF THE INVENTION

In-vivo imaging systems helpful in providing in-vivo imaging are known in the art. Autonomous in-vivo imaging devices, such as swallowable capsules, may move through or around a body lumen or body cavity, imaging as they move along. However, the direction or orientation of the in-vivo imaging device at the time that an image was acquired may be uncertain.

Furthermore, since a typical in-vivo imaging device may change direction and therefore image a specific location from more than one angle or location, it may be difficult for an operator of such an in-vivo imaging system to determine whether each particular location has been imaged one or more times etc. It may similarly be difficult for an operator to determine whether particular locations, such as hidden pathologies, have been imaged or imaged adequately.

Furthermore, it may be desirable to reconstruct three-dimensional information on a visualized object. Camera orientation information associated with each frame may be needed for such three-dimensional reconstruction.

Therefore it would be highly advantageous to have a system and method for determining the orientation of an in-vivo imaging device at the time of image acquisition.

SUMMARY OF THE INVENTION

There is provided, in accordance with an embodiment of the present invention, a system and method for determining the orientation of an in-vivo imaging device relative to the earth's gravitation field. Some embodiments may enable indication of specific locations where non-satisfactory imaging (coverage) was provided.

According to some embodiments of the present invention, a container or shell, such as a sphere or ellipse etc. with a non-transparent or visible orientation object or moveable unit, such as a ball, bubble, mass, etc., may be provided within an in-vivo imaging device, such as an autonomous capsule or other suitable device. The container or shell may be at least partially transparent and may contain, in addition to the orientation object, a filling, for example, comprising gas, liquid, paste, etc. The orientation object may be able to move or change location within the container. The object may reflect the orientation object's specific gravity relative to that of the container filling, if filling is used. The container may be placed in any suitable position where it may be viewed, at least partially or at least part of the time, by an imager. In this way, the location of the orientation object inside the container may be determined. By analyzing the image acquired by an imager, the in-vivo imaging device orientation relative to the earth's gravitational force may be determined for each acquired image. In some embodiments, two or more optical windows with accompanying containers and orientation objects, optionally facing opposite directions, may be used. Other in-vivo imaging devices having other structures may be used.

According to some embodiments of the present invention, a pendulum based orientation object may be incorporated into an in-vivo imaging device. This orientation object may be imaged by an in-vivo imaging device imager, such that the orientation of the in-vivo imaging device can be determined with reference to the position of the orientation object on the arc of the pendulum.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Unless specifically stated otherwise, as apparent from the following discussions, it is appreciated that throughout the specification discussions utilizing terms such as "processing", "computing", "calculating", "determining", or the like, may refer to the action and/or processes of a computer, workstation or computing system, or similar electronic computing device, that manipulate and/or transform data.

The word "orientation" as used herein may encompass the in-vivo imaging device direction or angle (relative to the gravitational field) at the time of acquiring an image. Orientation typically as used here does not include the overall position of the device, but rather the angle in which the device or certain components of the device face. Typically, orientation may be described by three angles, separate from three positional measurements in a six-degrees-of-freedom measurement. For example, the in-vivo imaging device may be at any angle from 0-360 degrees from the earth's gravitational field when acquiring an image. The word "orientation object" as used herein may encompass any suitable unit or object that may move, thereby indicating the orientation of a device relative to gravity. In some embodiments, the orientation object may be any suitable moveable unit, whose movement may be used to track device orientation. While some embodiments of the invention may be used to determine the orientation of a device, in other embodiments, other information may be determined, such as movement, activity, acceleration, etc.

Embodiments of the present invention may enable systems and methods to determine the orientation of an in-vivo imaging device relative to the earth's gravitation field. Knowledge of the orientation may enable determination of the direction of view of an in-vivo imaging device, such as an autonomous swallowable capsule that can obtain images of the entire gastrointestinal (GI) tract. Such a system and method may permit orientation determination when the in-vivo imaging device is located in areas that are large enough to permit changes in in-vivo imaging device orientation, such as the stomach or the large intestine etc. It may be noted that the in-vivo imaging device orientation relative to the gravitational field may change even in a smaller organs (e.g. the small intestine), although the orientation of the in-vivo imaging device relative to the organ in such cases may remain more stable. For example, due to the curvature of the small intestine, in-vivo imaging device orientation relative to the lumen may remain relatively constant, while the in-vivo imaging device orientation relative to the gravitation field may change as the imaging device moves along the lumen.

Embodiments of the device are typically autonomous and are typically self contained. For example, the device may be a capsule or other unit where all the components are substantially contained within a container or shell, and where the device does not require any wires or cables to, for example, receive power or transmit information The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Elements of in-vivo imaging device according to embodiments of the present invention, such as imaging components, illumination components, data transmission components, powering components etc. may be similar to embodiments described in PCT Application WO 01/65995 and/or in U.S. Pat. No. 5,604,531, each of which are assigned to the common assignee of the present invention and each of which are hereby incorporated by reference. Furthermore, receiving, processing and/or display systems suitable for use with embodiments of the present invention may also be similar to embodiments described in WO 01/65995 and/or in U.S. Pat. No. 5,604,531. Of course, devices and systems as described herein may have other configurations and other sets of components. A transmitter as used in certain embodiments of the present invention may typically operate using radio waves, but in some embodiments, such as those where the in-vivo imaging device is or is included within an endoscope, the transmitter may transmit via, for example, wire.

Figure 1:
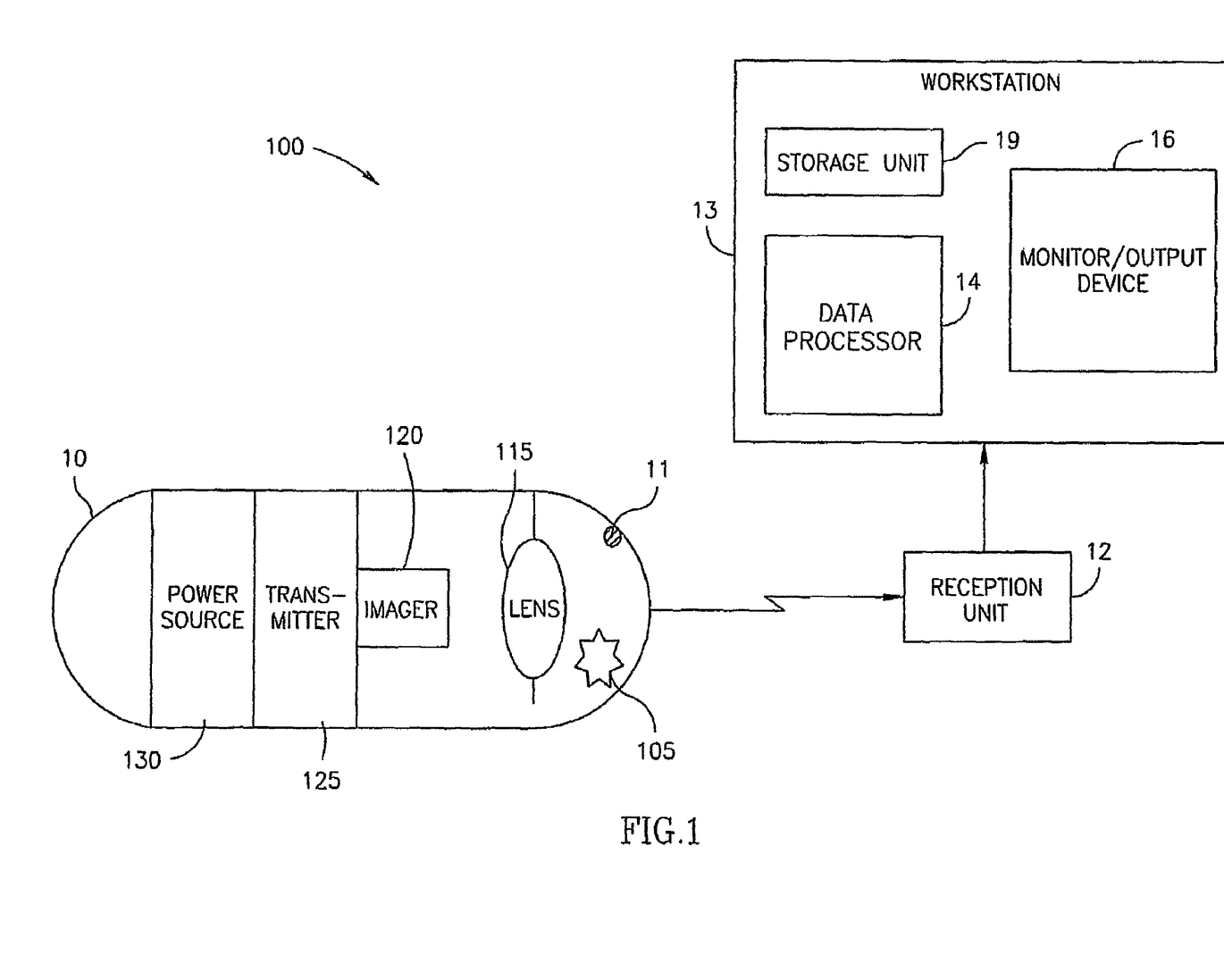
FIG. 1 is a schematic illustration of various components of an in-vivo imaging system, according to some embodiments of the present invention.

Reference is now made to FIG. 1, which illustrates components of an in-vivo imaging system 100, according to some embodiments of the present invention. As can be seen in FIG. 1, an in-vivo imaging device 10, such as a swallowable and autonomous capsule, may include an outer shell 31, a light source 105, lens 115, imager 120, transmitter 125 and power source 130. In-vivo imaging device 10 may be provided with an orientation object 11. Device 10 need not be swallowable and need not be autonomous; for example device 10 may be an endoscope. A data reception unit 12 may be provided for receiving in-vivo imaging device data. A data processor 14 may process data. Displaying apparatus 16, such as position monitors, image monitors or any other output devices may output data. For example, a data receiver unit 12 may receive data from in-vivo imaging device 10, and may thereafter transfer the data to data processor 14, and/or to data storage unit 19. The data or processed data may be displayed on a displaying apparatus 16. Data reception unit 12 may be separate from processing unit 14 or may be included within it. Data processor 14 may be, for example, part of a personal computer or workstation 13, and may include, for example, a processor, memory, software code etc. Alternatively, data processor 14 may be configured for real time processing and/or for post processing to be viewed or otherwise displayed at a later date. Data processor unit 14 may be incorporated into in-vivo imaging device 10. Units such as reception unit 12, data processor 14, monitor/output device 16, and storage unit 19 may be integrated into a single unit, or any combinations of the various units may be provided. Of course, other suitable components may be used. The orientation of device 10 may be displayed in various suitable manners on, for example, monitor/output device 16. While in some embodiments the structure and functioning of the receiving, processing and display systems or units are similar to those described in U.S. Pat. No. 5,604,531, other structures, functionalities and methods may be used. Of course, devices and systems as described herein may have other configurations and other sets of components.

Figure 2:
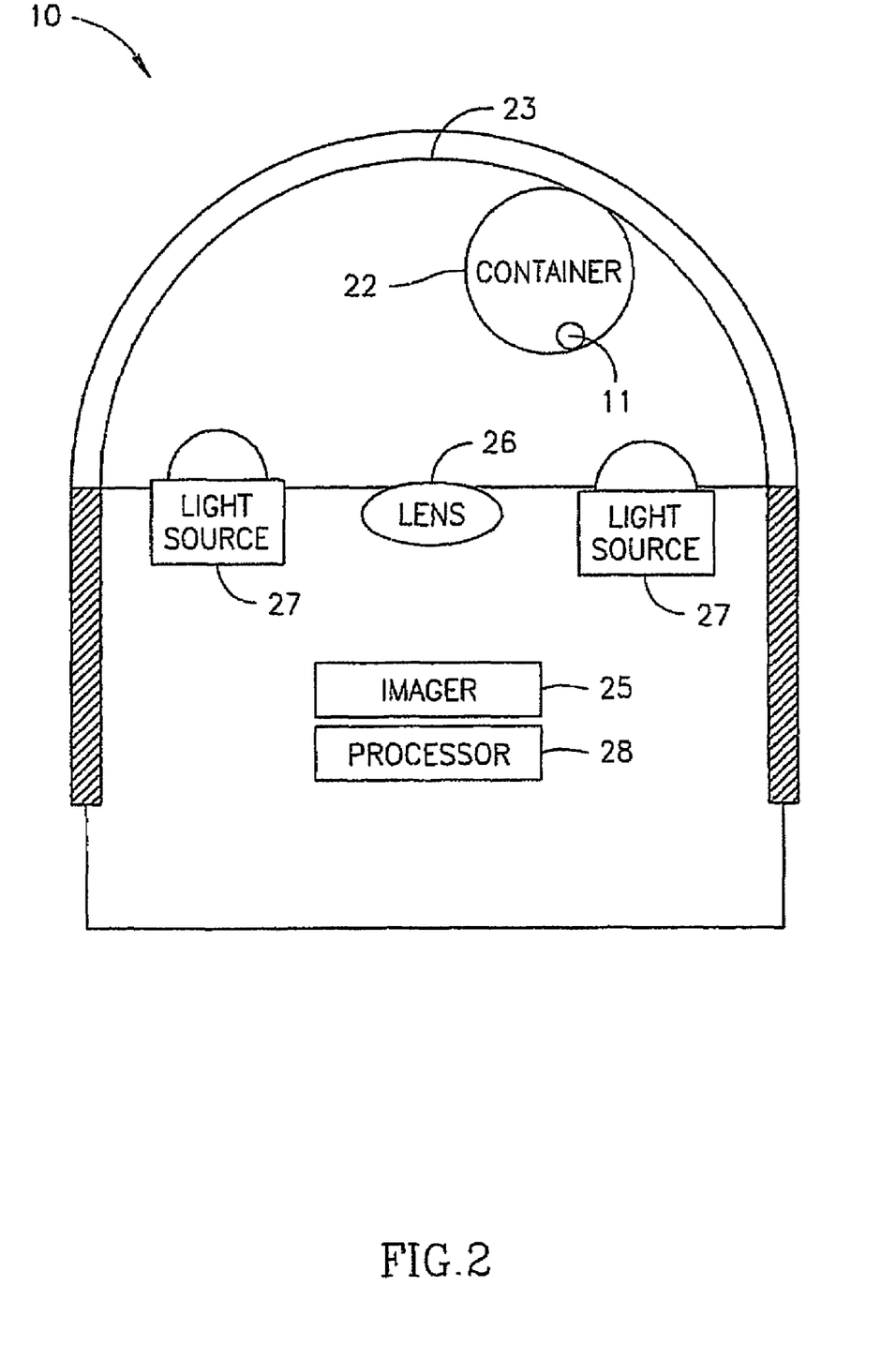
FIG. 2 is a graphical illustration of a container with an orientation object, which may be placed within an in-vivo imaging device, according to some embodiments of the present invention.
Figure 3A:
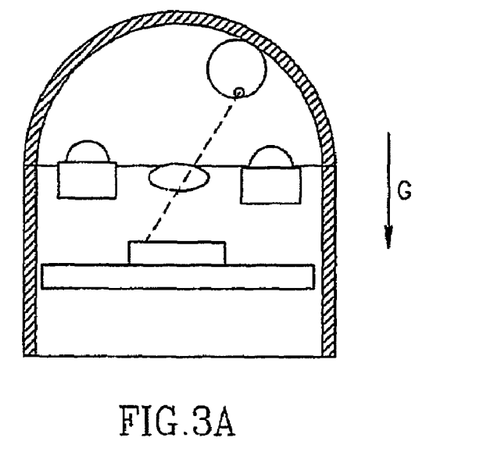
FIGS. 3A-3D illustrate examples of different orientations of in-vivo imaging devices, according to some embodiments of the present invention.
Figure 3B:
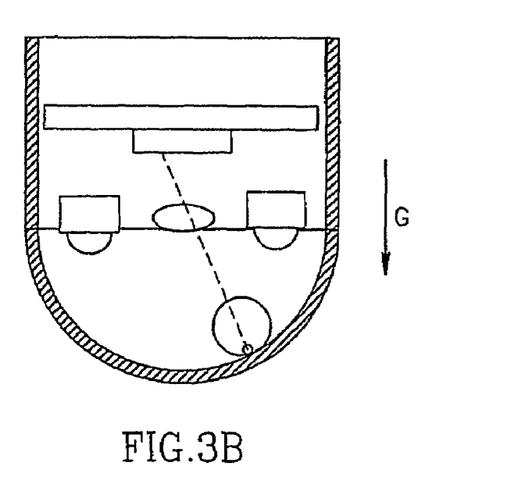
Figure 3C:
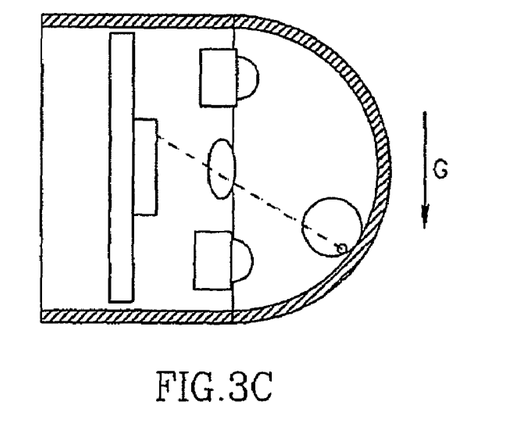
Figure 3D:
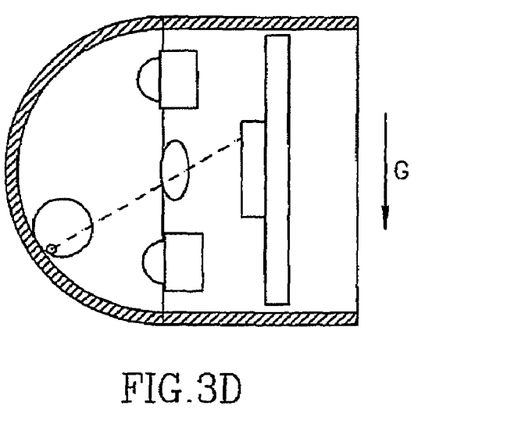

Reference is now made to FIG. 2, which is a schematic illustration of an in-vivo imaging device 10, according to some embodiments of the present invention, which may include an imaging apparatus, orientation determination apparatus, and a processing module etc. The imaging apparatus may include, for example, imager 25, lens 26, one or more light source(s) 27, and possibly other elements suitable to acquire, record, process, store and/or transmit etc. image data. Light source 27 may be similar to light source 105, or may be independent of light source 105. These elements may be similar to those described in U.S. Pat. No. 5,604,531 and/or PCT publication no. WO 01/65995.

An orientation determination apparatus, according to an embodiment of the invention, which may aid in determining an in-vivo imaging device orientation, may include: a shell or container 22, such as a sphere, ellipse or cone etc.; orientation object 11, such as a mass, bob, ball, weight, bubble, droplet or any other suitable moveable object or element; at least one optical dome 23 of in-vivo imaging device 10, wherein container 22 may be placed. According to another embodiment an optical dome 23 is not included. Furthermore, there may be no image of the outer world (for example, the intestine), however in-vivo imaging device orientation still may be determined. Shell or container 22 may be at least partially transparent and may be filled with air, gas, water, and/or other transparent or semi-transparent mediums. The processing module may include a processing unit 28, which may be incorporated into in-vivo imaging device 10, within, for example, imager 25, transmitter 125 (of FIG. 1), or any other suitable components. Processing unit 28 may be external to in-vivo imaging device 10, for example within data processor 14 (of FIG. 1). Processing unit 28 may include computing apparatus, such as an integrated circuit or any other apparatus for processing data, and software code, algorithms and any other suitable methods for implementing various transfers, storage, calculations, analyses, displays etc. of recorded data.

Shell or container 22 may be transparent or partially transparent, and orientation object 11 may typically be a moveable unit that is relatively small and relatively heavy or weighted so as to enable movement of orientation object 11 to various positions or locations (reflecting 360° mobility) in container 22, according to the angle at which in-vivo imaging device 10 is lying relative to earth 45. This ability of orientation object 11 to change location in container 22 may be due to orientation object 11 being of higher density than the container filling, and having a different specific gravity than the filling, or simply being loose inside a container filled with, e.g., gas, air, etc. Orientation object 11 may be non-transparent or partially non-transparent, or at least visible, such that it may be imaged by imager 25. Container 22 may be, for example, a two-dimensional or three-dimensional analogue of a circle, ellipsoid, or any structure that may provide unique dependency between the orientation and the location of object 11. Using a sphere, for example, all points on the outer boundary of the container 22 may be equidistant from a fixed point (e.g., the center), such that orientation object 11 may tend to slide or roll etc. to the lowest part of container 22, in accordance with gravitational force. In this way, images acquired by imager 25 that include orientation object 11 may be used to determine in-vivo imaging device 10 orientation relative to the earth's gravitational field for each image acquired. The orientation determination apparatus, such as container 22, may be positioned inside optical dome 23, and/or is typically within the field of view of imager 25. Typically, the imager 25 collects images via the optical dome 23, and imager 25 typically is configured to image areas external to the imaging device 10, in addition to imaging the orientation object 11. An optical dome need not be used. While in some embodiments container 22, such as a sphere, may extend in 3 dimensions, in other embodiments the container may be relatively flat, allowing orientation object 11 movement in only 2 dimensions. Alternatively, in other embodiments, container 22, such as sphere, may be placed in any suitable position where it may be viewed, at least partially or at least part of the time, by imager 25. Container 22 may be of other shapes, or may contain orientation objects of other shapes.

The location of orientation object 11 inside container 22 may be determined by, for example, simple viewing, or by for example, a processing unit, which may be located inside in-vivo imaging device in-vivo device 10. For example, a processor 28 may be provided within in-vivo imaging device 10. A processor may additionally or alternatively be provided externally to device 10, such as in data processor 14. Orientation object's location may be established by analyzing the location of the orientation object 11 relative to imager 25.

Reference is now made to FIGS. 3A-3D, which illustrate different orientations of in-vivo imaging device 10, such as a swallowable capsule, and corresponding orientations of orientation object 11 in container 22. The dashed lines in FIGS. 3A-3D indicate location of orientation object's 11 image on the imager 25. As can be seen in the figures, the orientation object 11 typically gravitates to the lowest point within container 22, unrelated to the orientation of the in-vivo imaging device 10. Furthermore, the image, angle and size etc. of orientation object 11 on imager 25, may be a function of the location of orientation object 11 inside container 22, information on the size of orientation object 11, the size, shape and location of the container relative to lens 26, the characteristics of lens 26, etc. Therefore by analysis of the image acquired by the imager 25, which includes orientation object 11, an operator of in-vivo imaging device workstation 13, for example, may determine the in-vivo imaging device 10 orientation, relative to the earth's gravitational field, for each image acquired.

Figure 4A:
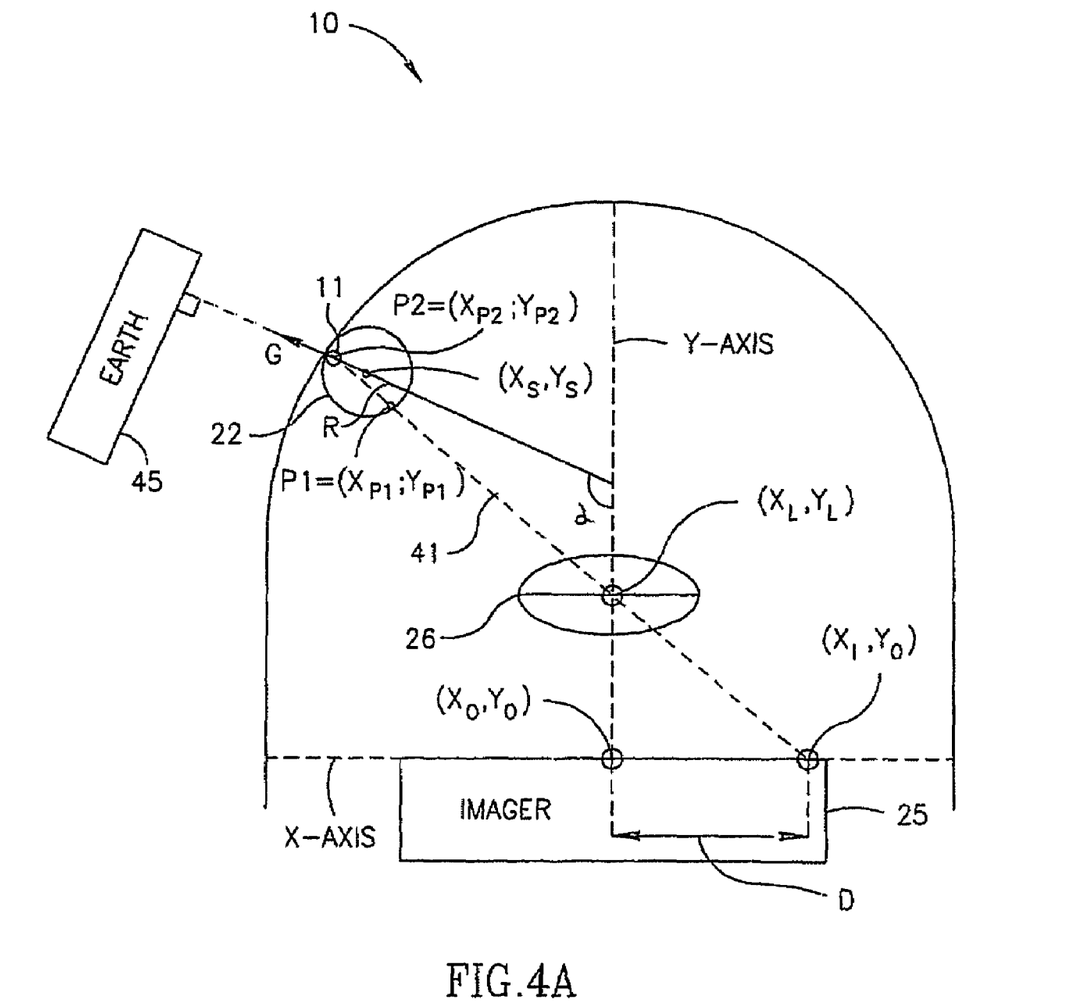
FIGS. 4A-4B are graphical illustrations of different coordinates useful in the calculation of orientation objects in an in-vivo imaging device, according to some embodiments of the present invention.

Reference is now made to FIG. 4A. The orientation of in-vivo imaging device 10 may be determined according to the precise location of the orientation object 11, which may relate to the gravitational force (G) at any given tine. Upon establishing the precise location of orientation object 11, the angle of in-vivo imaging device 10 relative to earth 45 may be determined, using gravitational force (G). This angle is hereinafter referred to as alpha ($\alpha$) FIG. 4A illustrates an example of two potential orientation objects, P1 and P2, in container 22, to indicate the case where it is uncertain upon initial calculation if orientation object 11 is on the near or far side of container 22. Any number of orientation objects may be present, at any locations within container 22. The measurement of the location of possible orientation objects may be attained through a straight line extending from the center of the relevant orientation object traveling through the center of the lens (e.g., on the Y axis). As can be seen in FIG. 4A, since the coordinates at the center of the lens are known ($X_L, Y_L$), and the coordinates of the center of the imager are known (this point may be the origin of the X and Y axis, represented by coordinates ($X_0, Y_0$)), the distance D may be measured. Once the position of the image of the orientation objects P1 or P2 on imager 25 is known, for example, according to distance D, the matching location of orientation object 11 (such as P1 and P2) inside sphere 22 may be further calculated.

For example, as can be seen with reference to FIG. 4A, the center of container 22 is located at ($X_S, Y_S$), with radius R, which are both known. The image of the orientation object 11 (e.g., P1 or P2) may be located on the imager at coordinate ($X_1, Y_0$), as determined above (which may be measured, and is equal to distance D). The angle $\alpha$, which is between the gravity force (G) and the in-vivo imaging device Y-axis is not known, and therefore needs to be calculated. The angle $\alpha$ may be determined by knowing the precise location of orientation object 11, which is the point of intersection of the image line 41 and the container 22, and measuring the angle between orientation object 11 and the gravitational force (G). According to one embodiment, an expression for the line that crosses the imager at $(X_1, Y_0)$, the center of the lens at $(X_L, Y_L)$ and the orientation object, can be determined as follows:

$$Y = -(Y_L/X_1)X + Y_L \qquad (a)$$

Other suitable formulae or calculations may be used. Since the orientation object is located inside the sphere (for example, a two-dimensional circle as shown in the figure, although a three-dimensional object may also be utilized), an expression for the circle can be written as:

$$(X-X_S)^2 + (Y-Y_S)^2 = R^2 \qquad (b)$$

Other suitable formulae or calculations may be used. By substituting (a) into (b), a second-degree equation having, for example, two possible solutions may result. The two solutions, for example, may be $(X_{P1}, Y_{P1})$ (1) and $(X_{P2}, Y_{P2})$ (2). These two solutions may correspond, for example, to two possible locations of orientation objects P1 and P2 inside container 22. For example, orientation object P1 may be closer than orientation object P2 to lens 25, and may therefore generate a larger imager on imager 25.

Figure 4B:
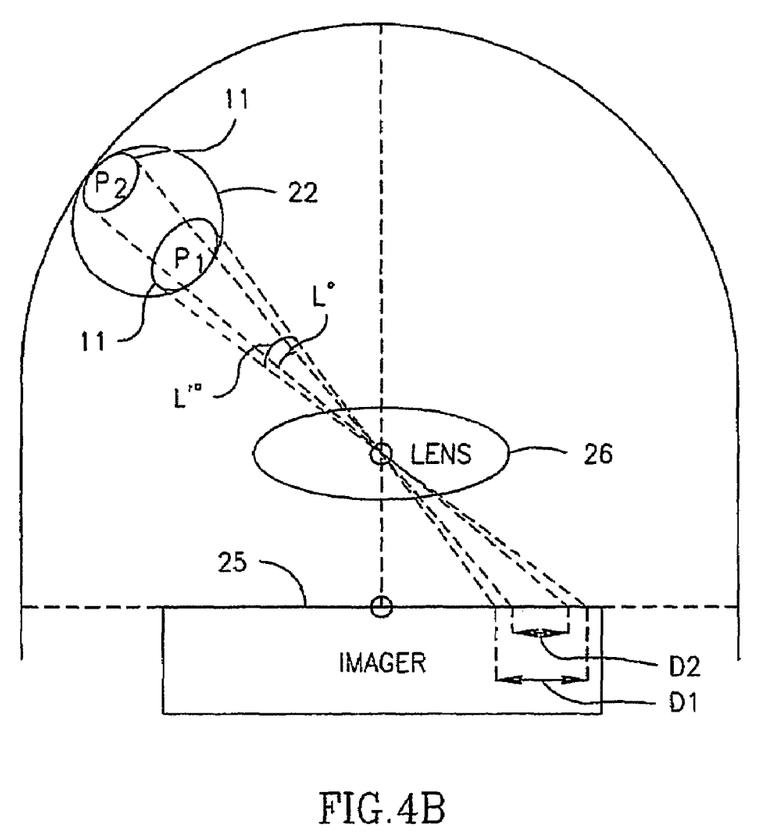

As can be seen with reference to FIG. 4B, by comparing the size of the respective images of the orientation objects, it may be determined whether an orientation object is, for example, at the near or far side of container 22. The respective sizes of orientation objects P1 and P2 may be calculated, for example, by measuring the sizes of the images of the respective orientation objects on imager 25, for example, D1 and D2. The respective sizes of orientation objects P1 and P2 may additionally or alternatively be calculated, for example, by measuring angular sizes of the respective orientation objects, according to the deflection angles L'° and L°, as seen in FIG. 4B. Of course, other orientation analyses may be used. Once the precise location of the orientation object 11 has been determined, for example by calculating the size of the imaged orientation object, the angle α may be calculated using, for example, the tangent (tg) of α. For example:

$$tg\alpha = (X_S - X_0)/(Y_S - Y_0)$$

$$\text{therefore } \alpha = tg^{-1}(X_S - X_0)/(Y_S - Y_0))$$

Other suitable formulae or calculations may be used. Processor 14 may therefore use the measured size information, together with location information of the orientation object 11 inside container 22, and other parameters to determine the orientation of in-vivo imaging device 10 in relation to gravity, for each image acquired. An operator may use this information to more accurately analyze and/or display in-vivo images, determine in-vivo imaging device 10 movements and parameters, and determine particular locations, such as hidden pathologies, where inadequate image coverage was attained. For example, an operator of system 100 may use such orientation information to order all images being displayed such that all images appear to be acquired from an in-vivo imaging device traveling through the inner body in a fixed direction etc. Even though the above calculations have been provided for the two-dimensional container depicted in FIGS. 4A and 4B, calculations to determine the orientation of an orientation object in a three-dimensional container may similarly or otherwise be calculated.

Figure 5:
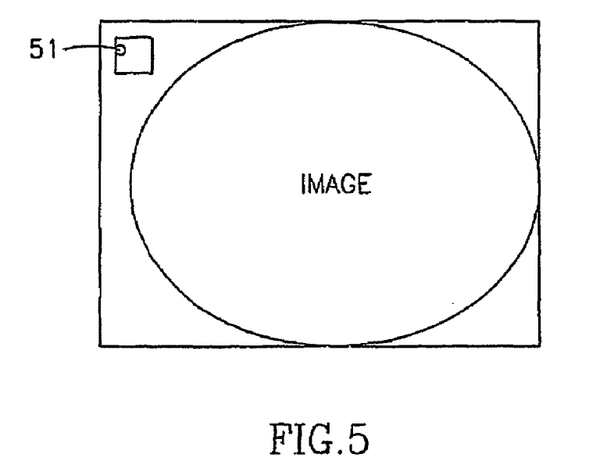
FIG. 5 is a schematic illustration of an example of the field of view of an in-vivo imaging device, which includes an orientation object, according to some embodiments of the present invention.

As can be seen with reference to FIG. 5, container 22 may be positioned in such a way as to minimize obstruction to the acquired images, such as in the corner 51 of the viewer (e.g., optical window frame) that is not in use, such that container 22 may be imaged by imager 25, yet not unduly disrupt clarity of acquired images. This may be achievable, for example, by designing the optics or positioning the orientation detection components to move or deflect the orientation object image to the image corner. Container 22 may be relatively small so as to provide minimal interference with acquired images. For example, in a device 10 that is 11 mm wide and 25 mm long, a container 22 may be less than 1 mm in diameter. Any other sizes of devices, containers, and orientation objects may be used. Container 22 may typically be fixed or stationary; in some embodiments container 22 need not be included. In-vivo imaging device dome 23 may be used as part of or instead of container 22. In such a case, orientation object 11 may move along the dome curvature as determined by the in-vivo imaging device orientation relative to the gravitational field. This may work for cases when the in-vivo imaging device faces down.

In some embodiments, two or more optical windows 23 with accompanying containers 22 and orientation objects 11, optionally facing opposite directions, may be used. An in-vivo imaging device with two optical windows may be similar to that described in U.S. patent application Ser. No. 10/046, 541, publication no. US-2002-0109774-A1, titled "SYSTEM AND METHOD FOR WIDE FIELD IMAGING OF BODY LUMENS", to the same assignee, which is incorporated by reference in its entirety. Such a usage of a plurality of orientation objects 11 may enable at least one of the heads to be facing down at all times, thereby enabling orientation determination.

According to some embodiments of the present invention, container 22 may contain or be filled with a liquid, optionally leaving a portion of the container liquid-free, for example, forming an air bubble. In this way, the liquid free content, such as an air bubble, may float to the highest area of the container at all times, thereby displaying a direct connection to the earth's gravitational force at all times. The air bubble may therefore function as orientation object 11, which may be used to determine orientation of an in-vivo imaging device 10 relative to gravity. Any other suitable objects or materials etc. may be placed in the container or used for the orientation object.

According to one embodiment of the present invention, more than one orientation object may be present in a container. For example, a ball and a bubble may be present in a sphere, such that at any given time, the ball will gravitate to the lowest point, while the bubble will rise to the highest point. Such an embodiment may enable an in-vivo imaging device to record both these orientation objects simultaneously, and may enable a processor to process both these images to provide relevant in-vivo imaging device orientation data. In other embodiments, multiple orientation objects, each moving on a different axis, may be included.

Figure 6:
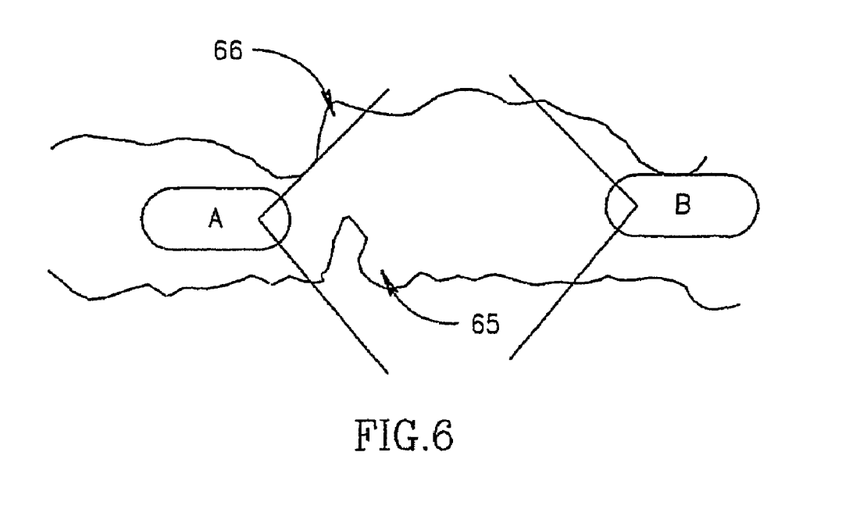
FIG. 6 illustrates an example of a pathology that may be hidden from an in-vivo imaging device from one angle, yet viewable by the in-vivo imaging device from another angle, according to one embodiment.

According to some embodiments of the present invention, an operator may determine non-satisfactory coverage of specific in-vivo locations. FIG. 6 illustrates an example of a "hidden pathology" that may be hidden from an in-vivo imaging device from one angle, yet viewable by the in-vivo imaging device from another angle, possibly indicating a non-satisfactory coverage of such a "hidden pathology". For example, as can be seen in FIG. 6, an intestinal fold, if viewed from a single direction by an in-vivo imaging device facing direction (A), may hide pathologies 65 and 66. In the case where the in-vivo imaging device subsequently faces the opposite direction, such as indicated by an autonomous capsule facing direction (B), pathologies 65 and 66 may be observed. In-vivo imaging system software, for example, working on data processor 14, may utilize orientation information (for example, as described above) to, for example, determine that images acquired by in-vivo imaging devices facing direction (A) and (B) were acquired when the in-vivo imaging device was facing opposite directions.

Analyses of such images may therefore enable determination, for example, that due to the in-vivo imaging device rotation or twin imagers of the in-vivo imaging device (such as from a two-sided autonomous capsule), two views of pathologies 65 and 66 should have been acquired. If one view only was acquired, for example from capsule facing direction (B), it may be determined that in-vivo imaging device 10 observed locations 65 and 66 retroactively only. Pathologies 65 and 66 may be indicated and marked, and optionally defined as having had non-satisfactory coverage, for example indicating a "hidden pathology". According to some embodiments of the present invention, a two-sided in-vivo imaging device may be used, thereby enabling pathologies to be more readily imaged from alternative angles. Determination of the orientation of such an in-vivo imaging device may enable definition of exposed pathologies, under-exposed pathologies etc. Data processor 14 may enable manipulation of an image stream acquired by device 10, for example, backwards, forwards, pausing, image selection, etc.

Figure 7:
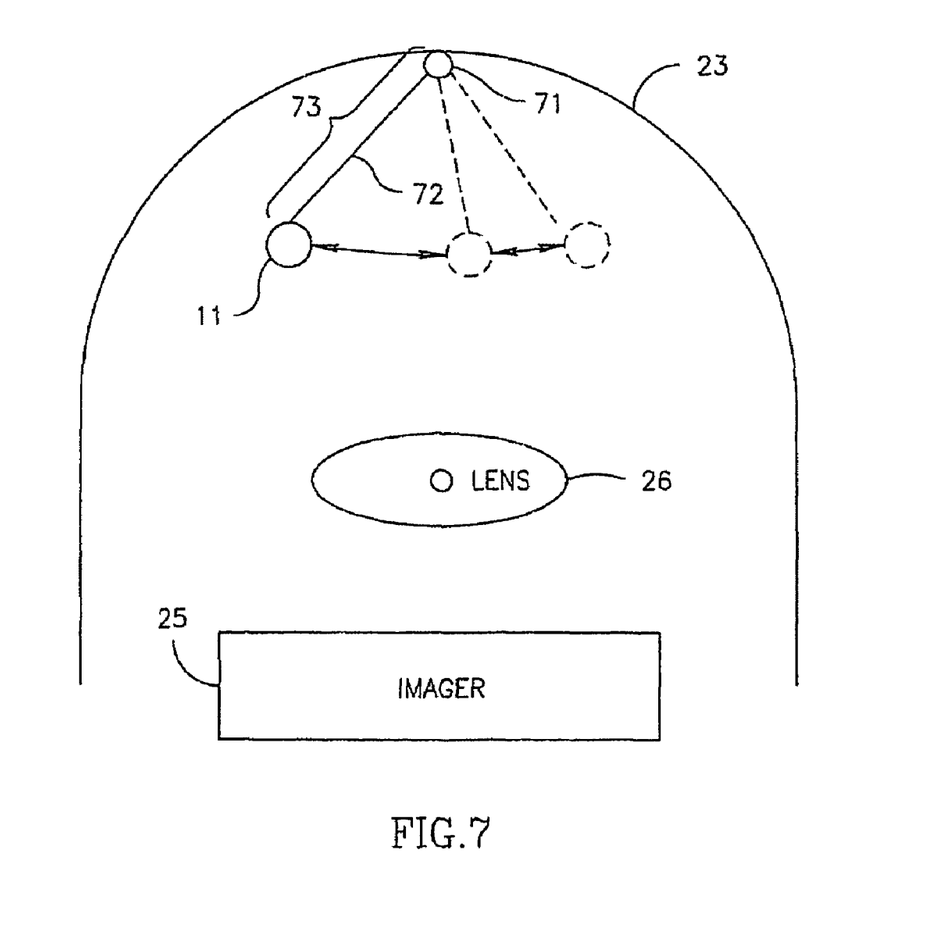
FIG. 7 illustrates an example of a pendulum-based orientation object integrated into an in-vivo imaging device, according to some embodiments of the present invention.

According to some embodiments of the present invention, as can be seen with reference to FIG. 7, orientation object 11, such as a mass, bob, ball etc., may be suspended from a fixed point 71 or fixed support, by a movable element such as a thread 72 or other connecting elements or devices. In this way, orientation object 11 may swing in an arc (for example, by using a thread or in a suspension) determined by the orientation object's 11 momentum and the force of gravity, thereby acting as a pendulum 73. Determination of the orientation object's 11 location on such an arc, according to an image of the orientation object's image on imager 25, may indicate the in-vivo imaging device's 10 direction and/or orientation relative to gravity. In some embodiments pendulum 73 may have a 3-dimensional ark, enabling suspended object to move in multiple directions. More than one pendulum may be provided, for example, one pendulum on each side of a two-headed autonomous capsule. In this case, at least one pendulum will respond to the force of gravity at all times. In other embodiments pendulum 73 may have a relatively flat arc, allowing orientation object 11 movement in only 2 dimensions. Optionally, pendulum 73 may be placed in a container such as 22 of FIG. 2.

Figure 8:
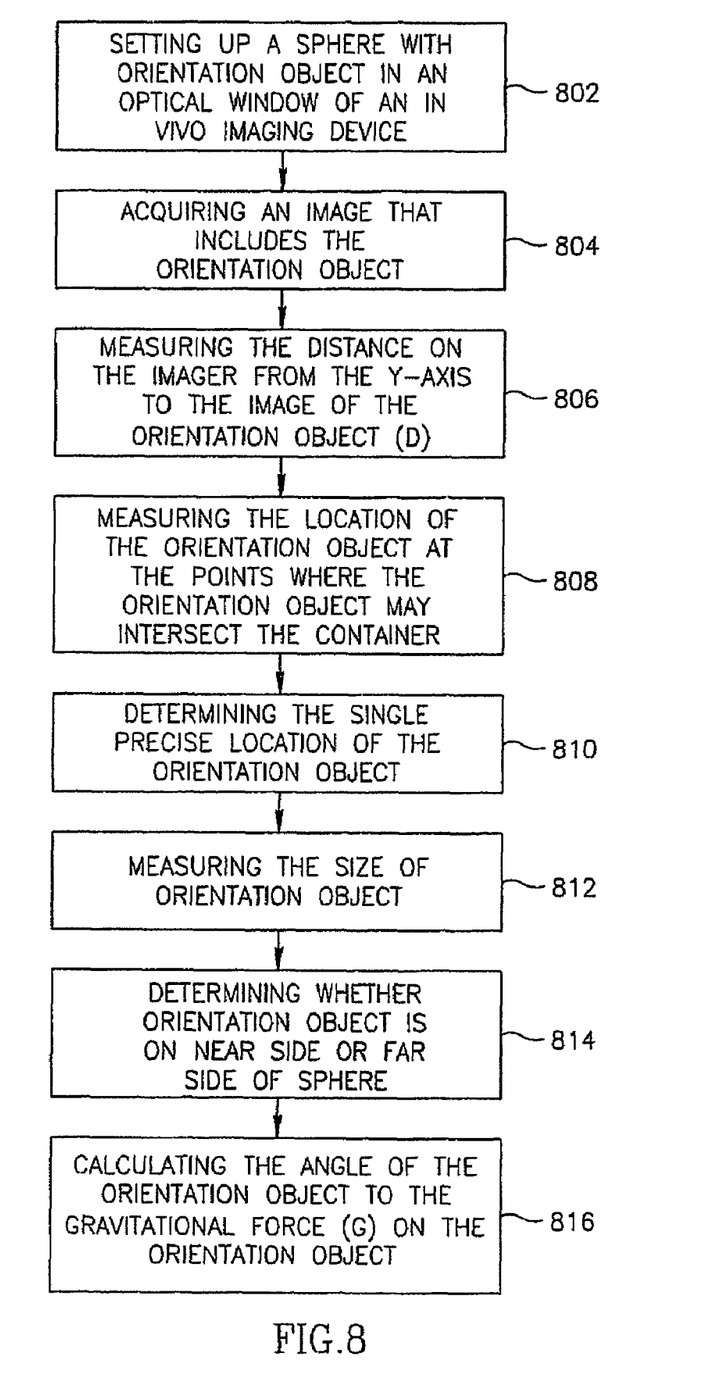
FIG. 8 is a flow chart illustrating a method for calculating in-vivo imaging device orientation, according to some embodiments of the present invention.

Reference is now made to FIG. 8, which illustrates a typical process for determining the orientation of an in-vivo imaging device relative to the earth's gravitation field, in accordance with an embodiment of the invention. As can be seen in FIG. 8, determination of an in-vivo imaging device's orientation relative to the earth's gravitational field may include setting up a container such as a sphere (the container may have another shape, or need not be used), with an orientation object in at least one optical window of an in vivo imaging device (802). At least one image may be acquired, which includes an orientation object (804). In some embodiments, merely viewing the object in an image may provide orientation or other information, but in other embodiments, calculations may be used. The distance (D) on the imager from the Y-axis to the image of the orientation object may be measured (806). The location of the orientation object at the points where the orientation object may intersect the container may be measured (808). The location of the orientation object may be determined (810). If there is more than one possible location corresponding to two points where the orientation object may intersect the container, the precise location may be determined, for example, by measuring the size of the orientation object (812), and determining whether the orientation object is on the near side or the far side of the sphere (814). The angle of the orientation object to the gravitational force (G) may be calculated (816), according to the precise location of the orientation object. Orientation of an in vivo imaging device may thereby be determined relative to the earth's gravitational field, for each frame acquired. Any combination of the above operations may be implemented. Further, other operations or series of operations may be used.

According to some embodiments of the present invention, a plurality of image frames that include image data of orientation object 11 may be analyzed. In the case where a plurality of frames are compared, for example, derivation of in-vivo imaging device acceleration may be enabled. Such analyses and/or comparisons may further enable determination of in-vivo locations that receive non-satisfactory imaging coverage. For example, the analyses of multiple frames may indicate hidden pathologies 65, 66, as can be seen in FIG. 6, which by nature of their location in a body lumen, have been inadequately exposed in the acquired images.

According to some embodiments of the present invention, in-vivo imaging device 10 acceleration may be determined according to location of orientation object 11 inside container 22. An algorithm may, for example, enable calculation of an orientation object 11 orientation during quiet periods, and thereby enable determination of in-vivo imaging device acceleration in these quiet periods. "Quiet periods" may be defined as the periods when the in-vivo imaging device does not move, or moves relatively little. Quiet periods may occur when the in-vivo imaging device does not move relative to the body, even though the body may move together with the in-vivo imaging device. Such movement may be detected by an analysis of consecutive images, which may be referred to as "image motility" analysis. Such an analysis is described, for example, in embodiments in PCT patent application PCT/IL02/00386, publication no. WO02/102223, by a common assignee, which is hereby incorporated by reference in its entirety. In the case where no in-vivo imaging device movement is detected relative to the lumen, according to the image motility analysis, the period may be considered to be a quiet period. It may therefore be assumed, in such a period, that the location of the orientation object 11 (or another structure, e.g., pendulum) is determined only by the gravitational field, and therefore the in-vivo imaging device's orientation may be determined.

According to some embodiments of the present invention, determination of an in-vivo imaging device's orientation relative the earth's gravitational field for a plurality of frames may enable reconstruction of three-dimensional information of visualized objects.

It will be appreciated that additional containers, pendulums and orientation objects may be integrated into in-vivo imaging device 10, for achieving various alternative functions; orientation need not be determined.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An in vivo imaging system comprising:
   an in-vivo device including at least an orientation indication apparatus and an imager configured to produce an image, wherein the orientation indication apparatus is positioned in the field of view the imager; and a processor, wherein said processor is configured to measure a size of said orientation indication apparatus and to calculate an angle of said orientation indication apparatus relative to the imager and to determine the orientation of the imager relative to gravitational force therefrom.

2. The system according to claim 1, wherein said orientation indication apparatus comprises a container.

3. The system according to claim 1, wherein said orientation indication apparatus comprises an orientation object.

4. The system according to claim 3, wherein said orientation object is selected from the group consisting of: a mass, a bob, a ball, a weight, a bubble and a droplet.

5. The system according to claim 3, wherein said orientation object is suspended from a fixed point.

6. The system according to claim 1, wherein said orientation indication apparatus is located in an optical dome, and wherein the imager collects images via the optical dome.

7. The system according to claim 1, wherein said orientation indication apparatus includes a viewable object.

8. The system according to claim 1 comprising a transmitter.

9. The system according to claim 1, wherein said in-vivo device is a swallowable capsule.

10. The device of claim 1, wherein the orientation indication apparatus is to indicate an orientation of the device relative to earth's gravitational force.

11. A system for determining orientation of an in-vivo device, said system comprising:

an in-vivo device, said in-vivo device including at least an orientation indication apparatus and an imager configured to produce an image wherein the orientation indication apparatus is positioned in the field of view the imager;

a reception unit; and a processor unit, wherein said processor unit is configured to measure a size of said orientation indication apparatus and to calculate an angle of said orientation indication apparatus relative to the imager and to determine the orientation of the imager relative to gravitational force therefrom.

12. The system according to claim 11, wherein said orientation indication apparatus includes an orientation object.

13. A method for determining orientation of an in-vivo device, the method comprising:

acquiring an image via an imager in an in-vivo device including at least an orientation indication apparatus and an imager, said image including at least the orientation object;

measuring the size of said orientation object; and calculating an angle of said orientation object relative to the imager and determining the orientation of the imager relative to gravitational force therefrom.

14. The method according to claim 13, comprising determining a location of said orientation object.

15. The method of claim 14, comprising analyzing a plurality of image frames, said image frames include image data of said orientation object.

16. The method according to claim 15, comprising indicating hidden pathologies based on said analyzing a plurality of image frames.

17. The method according to claim 14, comprising determining a location of said orientation object.

* * * * *

UNITED STATES PATENT AND TRADEMARK OFFICE
CERTIFICATE OF CORRECTION

PATENT NO. : 7,604,589 B2
APPLICATION NO. : 10/950694
DATED : October 20, 2009
INVENTOR(S) : Glukhovsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1026 days.

Signed and Sealed this

Fourteenth Day of December, 2010

David J. Kappos
*Director of the United States Patent and Trademark Office*